(12) United States Patent
Hickmann et al.

(10) Patent No.: US 9,856,199 B2
(45) Date of Patent: Jan. 2, 2018

(54) METHOD FOR PRODUCING MENTHONES FROM ISOPULEGOL IN THE GAS PHASE

(71) Applicant: BASF SE, Ludwigshafen (DE)

(72) Inventors: Volker Hickmann, Ludwigshafen (DE); Stefan Rüdenauer, Weinheim (DE); Martine Dehn, Ludwigshafen (DE); Andreas Keller, Speyer (DE); Stephanie Renz, Schwetzingen (DE); Daniel Schneider, Frankenthal (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/123,325

(22) PCT Filed: Mar. 6, 2015

(86) PCT No.: PCT/EP2015/054693
§ 371 (c)(1),
(2) Date: Sep. 2, 2016

(87) PCT Pub. No.: WO2015/132370
PCT Pub. Date: Sep. 11, 2015

(65) Prior Publication Data
US 2017/0066705 A1    Mar. 9, 2017

(30) Foreign Application Priority Data
Mar. 7, 2014 (EP) .................................... 14158373

(51) Int. Cl.
| | | |
|---|---|---|
| C07C 45/00 | (2006.01) | |
| B01J 23/00 | (2006.01) | |
| C07C 45/51 | (2006.01) | |
| A61K 8/35 | (2006.01) | |
| A61Q 11/00 | (2006.01) | |
| C07C 45/29 | (2006.01) | |
| A61Q 19/00 | (2006.01) | |
| B01J 23/889 | (2006.01) | |
| C07C 49/407 | (2006.01) | |

(52) U.S. Cl.
CPC .............. *C07C 45/512* (2013.01); *A61K 8/35* (2013.01); *A61Q 11/00* (2013.01); *A61Q 19/00* (2013.01); *B01J 23/8892* (2013.01); *C07C 45/29* (2013.01); *C07C 45/298* (2013.01); *C07C 49/407* (2013.01); *A61K 2800/10* (2013.01); *C07C 2601/14* (2017.05)

(58) Field of Classification Search
CPC .......................... C07C 45/512; B01J 23/8892
USPC ........................................................ 568/338
See application file for complete search history.

(56) References Cited

U.S. PATENT DOCUMENTS

| | | |
|---|---|---|
| 2,785,188 A | 3/1957 | Coe |
| 2,885,444 A | 5/1959 | Fookes et al. |
| 3,247,262 A | 4/1966 | Kaeding |
| 4,097,461 A | 6/1978 | Rutledge |
| 4,134,919 A | 1/1979 | Yamanaka et al. |
| 4,380,676 A | 4/1983 | Rasberger |
| 7,960,593 B2 | 6/2011 | Gralla et al. |
| 2006/0160719 A1 | 7/2006 | Emura et al. |
| 2013/0281696 A1 | 10/2013 | Schaub et al. |
| 2013/0324770 A1 | 12/2013 | Schaub et al. |
| 2013/0331607 A1 | 12/2013 | Schaub et al. |
| 2014/0018570 A1 | 1/2014 | Pazicky et al. |
| 2014/0018574 A1 | 1/2014 | Raith et al. |
| 2014/0024833 A1 | 1/2014 | Schelwies et al. |
| 2014/0024854 A1 | 1/2014 | Schaub et al. |

FOREIGN PATENT DOCUMENTS

| | | |
|---|---|---|
| DE | 4236111 A1 | 4/1994 |
| EP | 2706054 A1 | 3/2014 |
| WO | WO-2004056728 A1 | 7/2004 |
| WO | WO-2008016855 A1 | 2/2008 |
| WO | WO-2009013192 A1 | 1/2009 |
| WO | WO-2015086578 A1 | 6/2015 |

OTHER PUBLICATIONS

Gonzalez-Nunez, Maria Elena, et al., "Oxidation of Alcohols to Carboynl Compounds with CrO 3.SiO 2 in Supercritical Carbon Dioxide", The Journal of Organic Chemistry, vol. 71 No. 3 (Feb. 1, 2006), pp. 1039-1042, XP055113312, ISSN: 0022-3263, DOI: 10.1021/jo052137j.

Translation of International Preliminary Report on Patentability in PCT/EP2015/054693, Dec. 14, 2016.

U.S. Appl. No. 15/102,659, Schwartztrauber et al.

Bhattacharya, S., et al., "Periodic Trends in Charge Distribution for Transition-Metal Complexes Containing Catecholate and Semiquinone Ligands. Synthetic, Physical, and Stereodynamic Properties of the Tris(3,5-di-tert-butylquinone) Complexes of Ruthenium and Osmium", Journal of the American Chemical Society, vol. 112, No. 3, (1990), pp. 1088-1096.

Brunner, H., et al., "Enantioselective Catalysis; 150: [1] Chiral-at-Metal ($\eta^6$-p-Cymene)Ruthenium(II) Complexes of Binaphthyl Ligands—Synthesis, Characterization, and Enantioselective Catalysis", Synthesis 2003, No. 7, (2003), pp. 1091-1099.

Gladiali, S., et al., "Asymmetric transfer hydrogenation: chiral ligands and applications", Chemical Society Reviews, vol. 35, No. 3, (2006), pp. 226-236.

Hanyu, A., et al., "Selective Aerobic Oxidation of Primary Alcohols Catalyzed by a Ru($PPh_3$)$_3$$Cl_2$/Hydroquinone System", Tetrahedron Letters, vol. 39, No. 31, (1998), pp. 5557-5560.

Hartwig, J., et al., "Synthesis and Chemistry of Ruthenium Hydrido Aryloxides and Arylamides. An Investigation of Structure, N—H and O—H Elimination Processes, Proton-Catalyzed Exchange Reactions, and Relative Ru—X Bond Strengths", Organometallics, vol. 10, No. 6, (1991), pp. 1875-1887.

(Continued)

*Primary Examiner* — Sikarl Witherspoon
(74) *Attorney, Agent, or Firm* — Drinker Biddle & Reath LLP

(57) ABSTRACT

The present invention relates to a process for reacting isopulegol to menthone in the gas phase and to the use of the reaction products thus prepared as additives in foods, cosmetics, pharmaceutical products, tobacco formulations, household products, and laundry care products.

21 Claims, No Drawings

(56) References Cited

OTHER PUBLICATIONS

International Preliminary Report on Patentability with Annexes for PCT/EP2015/054453 dated Jun. 2, 2016.

International Preliminary Report on Patentability with Annexes for PCT/EP2015/054693 dated Jul. 4, 2016.

International Search Report for PCT/EP2015/054453 dated May 15, 2015.

International Search Report for PCT/EP2015/054693 dated Apr. 29, 2015.

Koelle, U., et al., "Bis(phenol) Adduct of Cp*Ru($\eta^5$-oxocyclohexadienyl), a Doubly Symmetrical Hydrogen-Bridged Ruthenium Complex", Organometallics, vol. 10, No. 8, (1991), pp. 2573-2577.

Kondo, T., et al., "Synthesis, Structure, and Reactivity of Novel Ruthenium(II) Phenolate Complexes", Organometallics, vol. 24, No. 5, (2005), pp. 905-910.

Munshi, P., et al., "Hydrogenation of Carbon Dioxide Catalyzed by Ruthenium Trimethylphosphine Complexes: The Accelerating Effect of Certain Alcohols and Amines", Journal of the American Chemical Society, vol. 124, No. 27, (2002), pp. 7963-7971.

Panichakul, D., et al., "A Rare $\eta^3$ Binding Mode of Aryloxides in Iridium, Rhodium, and Ruthenium Complexes", Organometallics, vol. 27, No. 24, (2008), pp. 6390-6392.

Treibs, W., et al., "Zur katalytischen Dehydrierung hydroaromatischer Verbindungen", Chemische Berichte der deutschen chemischen Gesellschaft (A and B Series), vol. 60, No. 10, (1927), pp. 2335-2341.

Yildiz, E., et al., "Synthesis of Ru(III) and Al(III) Complexes Containing Anthraquinone Moiety and Interactions of the UV Radiations", Asian Journal of Chemistry, vol. 21, No. 5, (2009), pp. 4047-4053.

Zhang, L., et al., "Ru-catalyzed 1,4-addition of arylboronic acids to acrylic acid derivatives in the presence of phenols", Chemical Communications, vol. 49, No. 78, (2013), pp. 8797-8799.

METHOD FOR PRODUCING MENTHONES FROM ISOPULEGOL IN THE GAS PHASE

CROSS-REFERENCE TO RELATED APPLICATIONS

This application is a national stage application (under 35 U.S.C. §371) of PCT/EP2015/054693, filed Mar. 6, 2015, which claims benefit of European Application No. 14158373.2, filed Mar. 7, 2014, both applications of which are incorporated herein by reference in their entirety.

The present invention relates to a process for reacting isopulegol to menthone in the gas phase and to the use of the reaction products thus prepared as additives in foods, cosmetics, pharmaceutical products, tobacco formulations, household products, and laundry care products.

BACKGROUND OF THE INVENTION

Menthol (1), the principal constituent of wild mint (*Mentha arvensis*), is among the most important aroma compounds in the fragrance and flavors industry and may take the form of four diastereomers. The oxidized diastereomers of menthol are referred to as menthone (2) and isomenthone (3), respectively. In the case of the diastereomers of menthone, the two alkyl substituents are in trans position; in the case of isomenthone, the substituents are in cis configuration.

On the basis of its odor and flavor profile, which is reminiscent of peppermint, menthone is employed in numerous formulations, for oral care and chewing gum applications, for example.

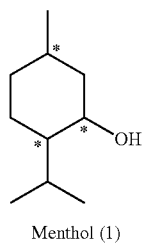

Menthol (1)

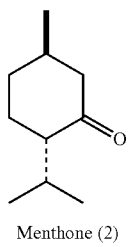

Menthone (2)

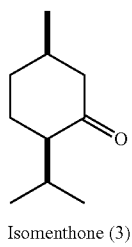

Isomenthone (3)

Menthone is customarily obtained by oxidation starting from menthol. Oxidizing agents used in this process are sodium chromate/sulfuric acid (*Spec. Chem.* 1987, 7, 193; *Acta Chem. Scand.* B 1979, 33, 148), sodium hypochlorite/acetic acid (*J. Org. Chem.* 1980, 45, 2030), ozone/ethyl acetate (JP 82180463) or pyridinium chlorochromate/silica gel (*Tetrahedron* 1979, 35, 1789). All in all, the oxidative methods for menthone preparation cannot be considered to be satisfactory, in view of the use of reagents which are of concern in relation to occupational hygiene and environmental compatibility.

DE 4236111 A1 describes a process for preparing menthone from menthol in a fixed-bed reactor, using a heterogeneous, copper-based dehydrogenation catalyst.

W. Treibs et al. (*Chem. Ber.* 1927, 60, 2335) describe the reaction of isopulegol (4) to menthone (2) in the presence of a catalyst which is obtained from copper acetate by precipitation with NaOH.

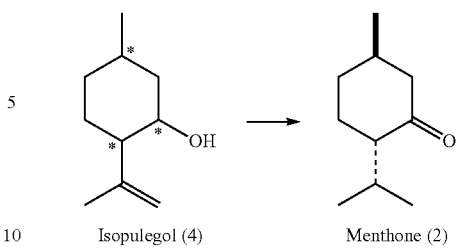

Isopulegol (4)    Menthone (2)

At a reaction temperature of 280° C., after the starting material has been passed over the catalyst, a mixture of menthone, isomenthone, and thymol can be isolated. The reaction regime disclosed therein is considered disadvantageous in view primarily of the awkward preparation of the catalyst and the high temperatures, which promote the formation of by-products.

Another means of preparing menthone, in this case starting from citronellol (5), is described in U.S. Pat. No. 4,134,919.

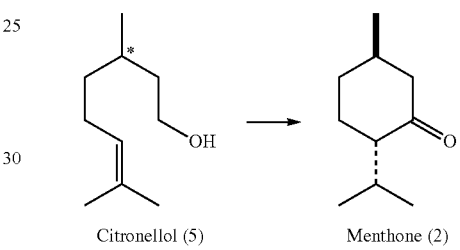

Citronellol (5)    Menthone (2)

Here, over the course of four hours, at temperatures of 150-260° C. and under continuous hydrogen pressure, citronellol is reacted to give a menthone/isomenthone mixture. Catalysts used are copper-based compounds, e.g., Cu/Cr, Cu/Al, or Cu/Zn. Isomenthone and menthone can also be obtained in enantiomerically enriched form. In that case enantiomeric excesses of not more than 80% are attained.

Citronellal (6) as well can be used as a starting material for preparing menthone. Forti et al. (*Synthesis* 2001, 1, 52) describe the cyclization of citronellal in the presence of calcium phyllosilicates, aluminum nitrate, and iron nitrate, and also of a solution of NaOH in dichloroethane. The product mixture contains menthone and isomenthone in a ratio of 69/31.

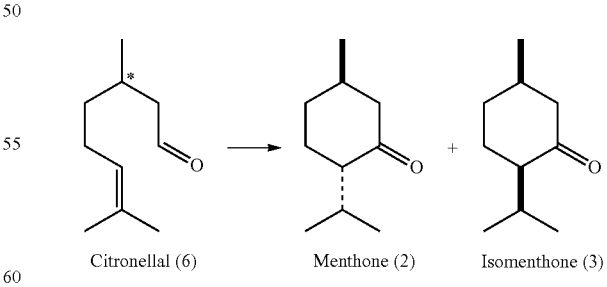

Citronellal (6)    Menthone (2)    Isomenthone (3)

In summary it is observed that the processes known from the prior art do allow the synthesis of menthone, even in enantiomerically enriched form, but entail the use of reagents which are harmful to health or the environment. Moreover, the processes disclosed only afford enantiomeric excesses of 80% at most. Moreover, the conduct of the reaction primarily in liquid reaction media, and the use of catalysts which are difficult to obtain, represent substantial disadvantages.

It is an object of the invention, therefore, to provide an improved process for the catalyzed preparation of menthone, in which menthone in particular is obtained with an increased fraction of one enantiomer, more particularly in enantiomerically pure form.

SUMMARY OF THE INVENTION

This object has been achieved by the process of the invention according to claim 1, more particularly by reaction of isopulegol, using an activated copper catalyst, more particularly an oxidic copper catalyst, and in particular by reacting isopulegol having an increased fraction of the enantiomer with (R) configuration in position 5, where isopulegol in the gas phase is contacted with a copper catalyst. In this process, prior to the reaction of isopulegol, the stated copper catalyst is contacted with hydrogen or, in particular, with hydrogen and an alcohol (added simultaneously or one after the other in any order), optionally in a carrier gas stream. After the reaction, the reaction product is optionally isolated.

An essential product of the reaction is menthone, which in particular has an increased fraction of the enantiomer with (R) configuration in position 5.

DETAILED DESCRIPTION OF THE INVENTION a) General Definitions

Absent Indications to the contrary, "isopulegol" encompasses the following possible stereoisomers:

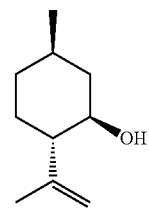
(1R,2S,5R)-(−)-Isopulegol

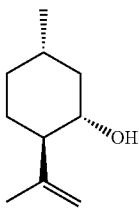
(1S,2R,5S)-(+)-Isopulegol

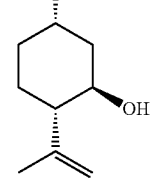
(1R,2S,5S)-2-Isopropenyl-5-methylcyclohexanol

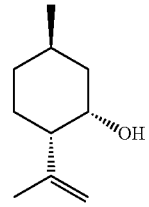
(1S,2S,5R)-2-Isopropenyl-5-methylcyclohexanol

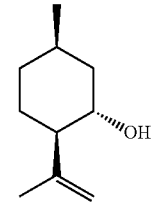
(1S,2R,5R)-2-Isopropenyl-5-methylcyclohexanol

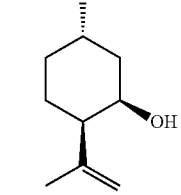
(1R,2R,5S)-2-Isopropenyl-5-methylcyclohexanol

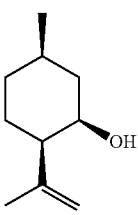
(1R,2R,5R)-2-Isopropenyl-5-methylcyclohexanol

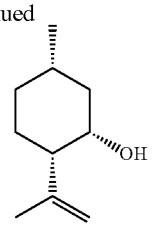
(1S,2S,5S)-2-Isopropenyl-5-methylcyclohexanol

Absent statements to the contrary, "menthone" encompasses the following two stereoisomers:

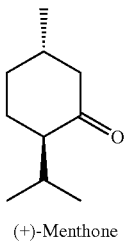
(+)-Menthone

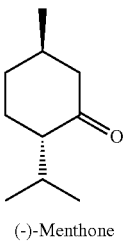
(−)-Menthone

Absent statements to the contrary, "isomenthone" encompasses the following two stereoisomers:

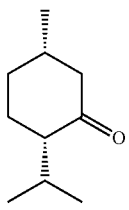
(−)-Isomenthone

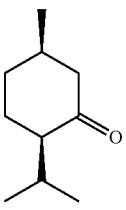
(+)-Isomenthone

"Enantiomercally pure" means that other than the specifically named enantiomer, no other enantiomeric form of the same chemical compound with at least one center of asymmetry is analytically detectable.

"Enantiomeric excess" Indicates the excess of an enantiomer in a mixture of enantiomers, and is calculated according to the following formula:

$$ee = [|m_1 - m_2|/(m_1 + m_2)] \times 100\%$$

ee: enantiomeric excess
$m_1$: fraction of enantiomer 1
$m_2$: fraction of enantiomer 2

"Monools" encompass alkanols, i.e., alkyl alcohols, and alkenols, i.e., alkenyl alcohols, having one hydroxyl group. The monools are primary or secondary, more particularly primary, monools.

"Polyols" encompass polyhydric analogs of the above monools, viz. alkanols, i.e., alkyl alcohols, and alkenols, i.e., alkenyl alcohols, having at least two, but more particularly more than two, hydroxyl groups. Diols encompass, in particular, alkanediols, i.e., dihydric analogs of alkyl alcohols, and alkenediols, i.e., dihydric analogs of alkenyl alcohols. "Alkyl" and "alkenyl" here are defined as indicated below. Preferred polyols, more particularly diols, are those which include at least one primary hydroxyl group. The other hydroxyl groups of the polyol are, in particular, either secondary hydroxyl groups or, with particular preference, are likewise primary hydroxyl groups.

Monools or polyols above may with preference also be referred to as "aliphatic polyols". "Alkyl" (or "alkane-" in the context of alkane-monools or alkane-polyols) stands in particular for saturated, straight-chain, or branched or cyclic hydrocarbon radicals having 1 to 20, 3 to 16, or 4 to 12 carbon atoms, such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl; and also n-heptyl, n-octyl, n-nonyl, and n-decyl, n-dodecyl, n-tetradecyl, n-hexadecyl, n-octadecyl, n-eicosyl, cyclobutyl, cyclopentyl, cyclohexyl, cycloheptyl, cyclooctyl, cyclononyl, cyclodecyl, cyclododecyl, cyclotetracyl, cyclohexadecyl, cyclooctadecyl, cycloeicosyl, and also be singly or multiply branched analogs thereof.

"Alkenyl" (or "alkene-" In the context of alkene-monools or alkene-polyols) stands in particular for the unsaturated, straight-chain, branched or cyclic analogs of the above alkyl radicals, and in particular has 2 to 30, 3 to 16, or 4 to 12 carbon atoms. These radicals may in particular be mono- or polyunsaturated, such as with 2-, 3-, 4-, or 5-fold unsaturation, more particularly monounsaturation. The double bonds here may be cumulative, conjugated, or nonconjugated.

"Aliphatic" radicals encompass, in particular, noncyclic, straight-chain or branched $C_{1-20}$ alkyl or $C_{2-20}$ alkenyl radicals, as defined above.

A "copper catalyst" encompasses compositions which comprise copper and are suitable for the catalysis and activation of the gas-phase reaction of the invention (reaction of isopulegol to menthone). Copper therein may take the form in particular of oxide. In particular, copper may be present in the +I and +II oxidation states. Besides copper, there may also be one or more of the elements aluminum, manganese, barium, chromium, calcium, or iron in the catalyst composition. In particular these elements may be present elementally or as oxides, examples being copper oxide, aluminum oxide, manganese oxide, barium oxide, chromium oxide, or iron oxide.

The elements aluminum, manganese, barium, chromium, calcium, or iron may in particular be in the +I to +VI oxidation states. Furthermore, there may be combinations of the elements copper, aluminum, manganese, barium, chromium, calcium, or iron present in the catalyst composition, in the form of "double" or "multiple" oxides, examples being dichromium copper tetraoxide, aluminum copper oxide ($Al_2CuO_4$), copper chromate, barium chromate, calcium silicate, or palygorskite. In the double or multiple oxides, the stated elements are present in particular in the +I to +VI oxidation states.

The "copper catalyst" may be supported or unsupported. Examples of support materials are quartz, silicon dioxide, aluminum oxide, or graphite.

The fraction of copper compounds in the catalyst is at least 20% up to 100%, based on the total weight of the dry catalyst. More particularly the fraction of copper compounds in the catalyst is 25% to 95%, as for example 30-65%, more particularly 30-45%, based on the total weight of the dry catalyst.

b) Specific Refinements

The present invention relates in particular to the following embodiments:

1. A process for reacting isopulegol, in which isopulegol in the gas phase is contacted with an activated copper catalyst, more particularly an oxidic copper catalyst, and optionally after the reaction a menthone-containing reaction product is isolated.

2. The process according to embodiment 1, in which the copper catalyst is activated, more particularly is activated with hydrogen or with hydrogen and an alcohol, preferably with hydrogen and an alcohol.

3. The process according to either of the preceding embodiments, in which the isopulegol used comprises an enantiomer of the formula I which is characterized by (R) configuration in position 5.

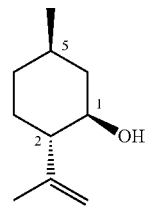

I

4. The process according to any of the preceding embodiments, in which the reaction is carried out at a temperature of 150-250° C., more particularly 160-200° C., e.g., 170° C. This process may be operated at 50 mbar to 1000 mbar or at up to 1 bar gage pressure. Preferred reduced-pressure regimes are 500 mbar even more preferred is the regime under atmospheric pressure.

5. The process according to any of the preceding embodiments, in which isopulegol is contacted with a copper-based catalyst.

This copper catalyst encompasses compositions which comprise copper and are suitable for the catalysis and activation of the gas-phase reaction of the invention. Copper therein may be present in particular in oxide form. More particularly, copper may be present in the +I and +II oxidation states.

Besides copper there may also be one or more elements selected from aluminum, manganese, barium, chromium, calcium, and iron present in the catalyst composition. More particularly these elements may be in elemental form or in the form of oxides, aluminum oxide, manganese oxide, barium oxide, chromium oxide, or iron oxide, together for example with copper oxide.

A further embodiment of the invention relates to a process for reacting isopulegol to menthone, in which isopulegol in the gas phase is contacted with an oxidic copper catalyst, optionally comprising at least one further element selected from aluminum, manganese, barium, chromium, calcium, and iron, and optionally after the reaction a menthone-containing reaction product is isolated, where the copper catalyst, before and/or during the reaction, Is activated with hydrogen and an alcohol.

The elements aluminum, manganese, barium, chromium, silicon, calcium, or iron may be present in particular in the +I to +VI oxidation states.

Furthermore, combinations of the elements copper, aluminum, manganese, barium, chromium, calcium, or iron may be present in the catalyst composition in the form of double oxides or multiple oxides, examples being dichromium copper tetraoxide, aluminum copper oxide ($Al_2CuO_4$), copper chromate, barium chromate, or palygorskite. In the double or multiple oxides, the stated elements are present in particular in the +I to +VI oxidation states.

The oxidic copper component of the catalyst composition is preferably copper oxide. The catalytically active components of the catalyst composition, optionally included additionally, are preferably selected from the compounds aluminum oxide, manganese oxide, aluminum copper oxide, chromium copper oxide, barium oxide, dichromium trioxide, chromium trioxide, copper chromate, barium chromate, calciumsilicate, and palygorskite, and mixtures thereof, especially mixtures containing 2, 3, 4, or 5 different compounds thereof. Especially preferred are compositions comprising copper oxide, aluminum oxide, manganese oxide, and aluminum copper oxide.

The copper catalyst may be supported or unsupported. Support materials are, for example, quartz, silicon dioxide, aluminum oxide, or graphite.

The fraction of copper compounds in the catalyst is at least 20% up to 100%, based on the total weight of the dry catalyst. In particular the fraction of copper compounds in the catalyst is 25% to 95%, e.g., 30-65%, especially 30-45%, based on the total weight of the dry catalyst.

In one embodiment of the invention, the catalyst has a composition comprising 30-40% copper oxide, 10-25% aluminum oxide, 10-25% manganese oxide, and 30-40% aluminum copper oxide, based in each case on the total mass of the dry catalyst.

Further examples of copper catalysts preferred in accordance with the invention include the commercial products X 540 T 1/8, E 406 T 1/8, Cu 1986 T 1/8, Cu 1808 T 1/8, Cu 1230 E1/16, or Cu 0865 T 3/16 of BASF Corporation (Florham Park, N.J. 07932, USA) having the following compositions:

X 540 T 1/8*
30.0-45.0 wt % copper oxide
30.0-40.0 wt % aluminum copper oxide ($Al_2CuO_4$)
10.0-25.0 wt % aluminum oxide
10.0-20.0 wt % manganese dioxide
E 406 T 1/8*
60.0-65.0 wt % chromium copper oxide ($Cr_2CuO_4$)
20.0-25.0 wt % copper oxide
5.0-10.0 wt % barium oxide
1.0-5.0 wt % graphite
1.0 wt % dichromium trioxide
1.0 wt % chromium trioxide
Cu 1986 T 1/8*
60.0-70.0 wt % chromium copper oxide ($Cr_2CuO_4$)
20.0-30.0 wt % copper oxide
1.0-5.0 wt % manganese dioxide
1.0-5.0 wt % silicic acid, sodium salt
1.0-5.0 wt % graphite
0.0-0.5 wt % copper chromate
Cu 1808 T 1/8*
55.0-65.0 wt % chromium copper oxide ($Cr_2CuO_4$)
20.0-30.0 wt % copper oxide
5.0-10.0 wt % silicon dioxide
5.0-10.0 wt % silicic acid, sodium salt
1.0-5.0 wt % graphite
Cu 1230 E 1/16*
41.0-46.0 wt % chromium copper oxide ($Cr_2CuO_4$)
25.0-35.0 wt % aluminum oxide
13.0-17.0 wt % copper oxide
10.0-13.0 wt % barium chromate
Cu 0865 T 3/16*
55.0-65.0 wt % copper oxide
25.0-35.0 wt % calcium silicate
5.0-10.0 wt % palygorskite ($[Mg(Al_{0.5}-1Fe_{0-0.5})]Si_4(OH)O_{10}.4H_2O$)
1.0-5.0 wt % graphite
1.0-5.0 wt % silicon dioxide
0.5-1.5 wt % silica (crystalline).
*all figures based on the total weight of the dry catalyst.

6. The process according to any of the preceding embodiments, in which the catalyst is used as a homogeneous or heterogeneous catalyst. The heterogeneous catalysis of the reaction of Isopulegol in a fixed-bed reactor, in particular, represents one preferred embodiment of the invention.

7. The process according to any of the preceding embodiments, in which the catalyst before the reaction is activated with hydrogen or with hydrogen and an alcohol (simultaneously or one before the other, in any order), optionally in a carrier gas stream.

The temperature for the activation can be between 150 and 220° C.

One preferred embodiment of the process is the activation of the catalyst first of all by a stream of hydrogen, which flows through the reactor, supported, in particular, by a stream of carrier gas. In a temporally offset step of the process, in this preferred embodiment, the reductive activation is followed by the activation of the catalyst by an alcohol, which is passed through the reactor with or without carrier gas assistance, more particularly without such assistance.

Another preferred embodiment of the process encompasses the temporally offset activation of the catalyst, initially by hydrogen, subsequently by an alcohol, with carrier gas added in none of the activation steps.

Another preferred embodiment of the process encompasses the activation of the catalyst initially by hydrogen, subsequently by alcohol, more particularly with addition of carrier gas in both activation steps.

Other specific refinements of the process of the invention encompass the temporally offset activation of the catalyst first by an alcohol, thereafter by hydrogen. Carrier gas may be added for example in one, in both, or in neither of the activation steps.

Furthermore, the simultaneous activation of the catalyst with hydrogen and with alcohol is another embodiment of the process of the invention. In that case the activation may be carried out for example with assistance by a stream of carrier gas, or without a stream of carrier gas.

The catalysts activated as described above may be kept under suitable solvents, especially aliphatic linear or branched alcohols, preferably isononanol.

8. The process according to any of the preceding embodiments, in which nitrogen or argon or mixtures thereof are used as carrier gas. In this case in particular the use of nitrogen is a preferred embodiment of the process. In particular the carrier gas-based flow traversal of the reactor during the reaction of the invention and during the activation of the catalyst represents one preferred embodiment of the process of the Invention. Furthermore, the carrier gas stream during the reaction may contain up to 10 vol %, such as 0.1 to 10 vol %, for example, of hydrogen.

9. The process according to embodiment 8, in which the flow through the reactor is at a rate of 0 to 5 NL/h carrier gas per g/h substrate, more particularly 0.5 to 1.5 NL/h carrier gas per g/h substrate.

10. The process according to any of the preceding embodiments, in which the alcohol used for the activation is selected from saturated or mono- or polyunsaturated, straight-chain or branched or cyclic, aliphatic or aromatic, more particularly saturated or mono- or polyunsaturated, straight-chain or branched aliphatic, monools or polyols, more particularly monools or diols, or combinations thereof.

11. The process according to any of the preceding embodiments, in which the alcohol used for the activation, more particularly alkanol or alkenol, comprises at least one primary and/or at least one secondary OH group.

This includes, for example, alcohols, more particularly alkanols or alkenols, which have one, two or three primary OH groups, preferably one primary OH group. It also includes alcohols, more particularly alkanols or alkenols, having one primary and one secondary OH group; alcohols, more particularly alkanols or alkenols, having two primary OH groups and one secondary OH group; alcohols, more particularly alkanols or alkenols, having one primary OH group and two secondary OH groups; and alcohols, more particularly alkanols or alkenols, having one, two or three secondary OH groups.

Preferred alcohols, more particularly alkanols or alkenols, are those having one primary OH group, two primary OH groups, or one primary and one secondary OH group.

In particular the use of alcohols having saturated or mono- or polyunsaturated, straight-chain or branched aliphatic hydrocarbon radicals, having 1 to 20 carbon atoms carbon atoms, represents a preferred embodiment of the invention. Particularly noteworthy are aliphatic $C_1$-$C_{20}$, $C_3$-$C_{16}$, or $C_4$-$C_{12}$ radicals. Among these, in particular, alcohols, more particularly alkanols or alkenols, in which condensation is unlikely under the reaction conditions, examples being 1,4-butanediol, hexanol, cyclohexanol, octanol, 1-nonanol, and citronellol, are a preferred embodiment of the invention.

The stated alcohols include, for example, monools or diols having three carbon atoms, examples being propan-1-ol, propan-2-ol, propane-1,2-diol, and propane-1,3-diol, and also monools or diols having four carbon atoms, such as, for example, butan-1-ol, butan-2-ol, 2-methylpropan-1-ol, butane-1,2-diol, butane-1,3-diol, butane-1,4-diol, butane-2,3-diol, 2-methylpropane-1,3-diol, and 2-methylpropane-1,2-diol.

The stated alcohols also include pentanols having at least one primary or one secondary OH group, such as, for example, the monools pentan-1-ol, pentan-2-ol, pentan-3-ol, 2-methylbutan-1-ol, 2-methylbutan-2-ol, 3-methylbutan-1ol, 3-methylbutan-2-ol, 2,2-dimethylpropan-1-ol, and the diols pentane-1,2-diol, pentane-1,3-diol, pentane-1,4-diol, pentane-1,5-diol, pentane-2,3-diol, pentane-2,4-diol, pentane-2,5-diol, and also the branched structural isomers thereof.

"Hexanol" Includes preferably the following monools having at least one primary or one secondary OH group: hexan-1-ol, hexan-2-ol, hexan-3-ol, 2-methylpentan-1-ol, 3-methylpentan-1-ol, 4-methylpentan-1-ol, 3-methylpentan-2-ol, 4-methylpentan-2-ol, 2-methylpentan-3-ol, 2,2-dimethylbutan-1-ol, 2,3-dimethylbutan-1-ol, 3,3-dimethylbutan-1-ol, 3,3-dimethylbutan-2-ol, and 2-ethylbutan-1-ol. Further included under "hexanol" are the diols 1,2-hexanediol, 1,3-hexanediol, 1,4-hexanediol, 1,5-hexanediol, 1,6-hexanediol, 2,3-hexanediol, 2,4-hexanediol, 2,5-hexanediol, and 3,4-hexanediol, and also the branched structural isomers thereof.

The stated alcohols also include heptanols having at least one primary or one secondary OH group, such as, for example, the monools heptan-1-ol, heptan-2-ol, heptan-3-ol, heptan-4-ol, 2-methylhexan-1-ol, 2-methylhexan-3-ol, 2-methylhexan-4-ol, 2-methylhexan-5-ol, 2-methylhexan-6-ol, 3-methylhexan-1-ol, 3-methylhexan-2-ol, 3-methylhexan-4-ol, 3-methylhexan-5-ol, 3-methylhexan-6-ol, 2,2-dimethylpentan-1-ol, 2,2-dimethylpentan-3-ol, 2,2-dimethylpentan-4-ol, 2,2-dimethylpentan-5-ol, 2,3-dimethylpentan-1-ol, 2,3-dimethylpentan-4-ol, 2,3-dimethylpentan-5-ol, 2,4-dimethylpentan-1-ol, 2,4-dimethylpentan-3-ol, 3,3-dimethylpentan-1-ol, 3,3-dimethylpentan-2-ol, 3-ethylpentan-1-ol, 3-ethylpentan-2-ol, 2,2,3-trimethylbutan-1-ol, 2,2,3-trimethylbutan-4-ol, and the diols heptane-1,2-diol, heptane-1,3-diol, heptane-1,4-diol, heptane-1,5-diol, heptane-1,6-diol, heptane-1,7-diol, heptane-2,3-diol, heptane-2,4-diol, heptane-2,5-diol, heptane-2,6-diol, heptane-2,7-diol, heptane-3,4-diol, heptane-3,5-diol, and also the branched structural isomers thereof.

"Octanol" includes preferably the following monools having one primary or one secondary OH group: octan-1-ol, octan-2-ol, octan-3-ol, octan-4-ol, 2-methylheptan-1-ol, 2-methylheptan-3-ol, 2-methylheptan-4-ol, 2-methylheptan-5-ol, 2-methylheptan-6-ol, 2-methylheptan-7-ol, 3-methylheptan-1-ol, 3-methylheptan-2-ol, 3-methylheptan-4-ol, 3-methylheptan-5-ol, 3-methylheptan-6-ol, 3-methylheptan-7-ol, 4-methylheptan-1-ol, 4-methylheptan-2-ol, 4-methylheptan-3-ol, 4-methylheptan-5-ol, 4-methylheptan-6-ol, 4-methylheptan-7-ol, 2,2-dimethylhexan-1-ol, 2,2-dimethylhexan-3-ol, 2,2-dimethylhexan-4-ol, 2,2-dimethylhexan-5-ol, 2,2-dimethylhexan-6-ol, 2,3-dimethylhexan-1-ol, 2,3-dimethylhexan-4-ol, 2,3-dimethylhexan-5-ol, 2,3-dimethylhexan-6-ol, 2,4-dimethylhexan-1-ol, 2,4-dimethylhexan-3-ol, 2,4-dimethylhexan-5-ol, 2,4-dimethylhexan-6-ol, 2,5-dimethylhexan-1-ol, 2,5-dimethylhexan-3-ol, 2,5-dimethylhexan-4-ol, 2,5-dimethylhexan-6-ol, 3,3-dimethylhexan-1-ol, 3,3-dimethylhexan-2-ol, 3,3-dimethylhexan-4-ol, 3,3-dimethylhexan-5-ol, 3,3-dimethylhexan-6-ol, 3,4-dimethylhexan-1-ol, 3,4-dimethylhexan-2-ol, 3-ethylhexan-1-ol, 3-ethylhexan-2-ol, 3-ethylhexan-4-ol, 3-ethylhexan-5-ol, 3-ethylhexan-6-ol, 2,2,3-trimethylpentan-1-ol, 2,2,3-trimethylpentan-4-ol, 2,2,3-trimethylpentan-5-ol, 2,2,4-trlmethylpentan-1-ol, 2,2,4-trimethylpentan-3-ol, 2,2,4-trimethylpentan-5-ol, 2,3,3-trimethylpentan-1-ol, 2,3,3-trimethylpentan-4-ol, 2,3,3-trimethylpentan-5-ol, 2,3,4-trimethylpentan-1-ol, 3-ethyl-2-methylpentan-1-ol, 3-ethyl-2-methylpentan-4-ol, 3-ethyl-2-methylpentan-5-ol, 3-ethyl-3-methylpentan-1-ol, 3-ethyl-3-methylpentan-2-ol, 3-ethyl-3-methylpentan-4-ol, 2,2,3,3-tetramethylbutan-1-ol. "Octanol" further includes the diols 1,2-octanediol, 1,3-octanediol, 1,4-octanediol, 1,5-octanediol, 1,6-octanediol, 1,7-octanediol, 1,8-octanediol, 2,3-octanediol, 2,4-octanediol, 2,5-octanediol, 2,6-octanediol, 3,4-octanediol, 3,5-octanediol, 3,6-octanediol, 4,5-octanediol, and also the branched structural isomers thereof.

Another preferred embodiment of the invention is represented by alcohols, more particularly alkanols or alkenols, the use of which promotes the preservation of the configuration of the stereocenter of position 5 of isopulegol, such as, in particular, 1-nonanol, 1,4-butanediol, and citronellol.

Especially preferred is the use of alcohols, more particularly alkanols or alkenols, having one primary OH group, examples being citronellol, 1-nonanol, or mixtures thereof, or of alcohols, more particularly alkanols or alkenols, having two primary OH groups, an example being 1,4-butanediol.

12. The process according to any of the preceding embodiments, in which the reaction of isopulegol is carried out in a gas-phase apparatus with coupled vaporizer. In that case the vaporizer is mounted, for example, above the reactor and serves to evaporate the liquid reaction components, more particularly isopulegol and the alcohol used optionally for the activation, and to heat the gas streams used, such as hydrogen, nitrogen or argon, for example, optionally, if not already preheated.

13. The process according to any of the preceding embodiments, in which the reaction product comprises menthone (2) and/or isomenthone (3).

In one preferred embodiment of the invention, menthone and isomenthone are the principal products, and, for example, menthol (1) and thymol (7) are obtained as by-products. In particular the reaction to menthone and isomenthone with (R) configuration of the stereocenter in position 5 is a preferred embodiment of the process of the invention.

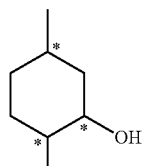
Menthol (1)

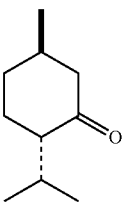
Menthone (2)

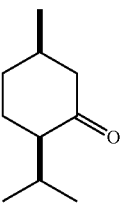
Isomenthone (3)

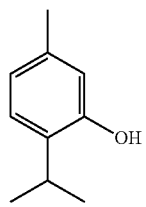
Thymol (7)

Especially preferred is a process in which the reaction product comprises menthone and/or isomenthone with an increased fraction, preferably more than 70%, more particularly more than 80%, very preferably more than 90%, e.g., at least 95%, 96%, 97%, 98%, 99%, or 99.9%, of the enantiomer with (R) configuration in position 5.

14. The process according to any of the preceding embodiments, in which menthone (8) and/or isomenthone (9) are present in substantially enantiomerically pure form in the reaction product.

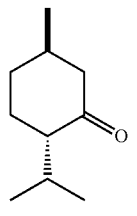
Menthone (8)

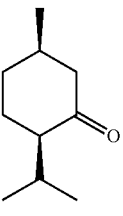
Isomenthone (9)

15. The use of a reaction product prepared according to any of the preceding embodiments as an additive in foods, cosmetics, pharmaceutical products, tobacco formulations, household products, and laundry care products.

c) Detailed Description of the Process of the Invention

The principle of the process of the invention is elucidated in more detail below, with reference to one preferred embodiment for the reaction of isopulegol.

The gas-phase apparatus comprises a reactor, which includes, for example, one or more tubes, which can be heated either electrically, with heat-transfer fluid, or with hot gases (e.g., flue gas). The fixed-bed catalyst is within the reactor, in one of the tubes, for example. In the catalyst bed the reaction temperature can be measured. The carrier gas, loaded with substrate, flows through the catalyst bed, from top to bottom for example. Coupled to the reactor is a vaporizer, which is mounted, for example, above the reactor and can be used to transfer the (liquid) reactants into the gas phase, optionally with support from use of carrier gas. The carrier gas stream as well may be heated by means of the vaporizer or by means of a separate preheater to the reaction temperature. On emergence from the reactor, the reaction products condense either spontaneously, by quenching with cold gas or liquid, or by condensation on cooled surfaces. The transition between vaporizer and reactor is well-insulated or even protectively heated (wrapped with a heating tape, for example) in order to prevent condensation.

In one specific embodiment, the gas-phase reactor is charged, for example, with a copper catalyst, e.g., X540T 1/8, and the catalyst is activated under an $H_2$-containing gas stream. The temperature for the activation may be between 150 and 220° C. Vaporizer and reactor are operated for example at a temperature of 150-220° C. under 50 mbar to 1000 mbar or up to 1 bar gage pressure. Preferred reduced-pressure modes are 500 mbar; the atmospheric-pressure regime is even more preferred, and using carrier gas, such as nitrogen or argon, for example, and optionally in the presence of up to 10 vol % of hydrogen. Isopulegol is introduced continuously into the vaporizer. The product mixture is condensed at the reactor exit, and the composition is analyzed by gas chromatography.

Following reaction (after 1 to 24, 1 to 20, 2 to 11, or about 5 hours, for example), reactor and vaporizer are cooled under a stream of carrier gas, and the reaction is continued, on the next day, for example, for one or more reaction cycles, without change of catalyst. Alternatively the reaction is carried out continuously without interruption. After defined reaction times in each case, for example, one hour, conversion rate, mass balance, and product composition are determined by way of gas chromatography. The products detected include, for example, menthone, isomenthone, thymol, and menthol.

Where enantiomerically enriched isopulegol is used as starting material in the implementation of the process of the invention, for example, it is additionally possible to detect a menthone/Isomenthone mixture in enantiomerically enriched form. The enantiomeric excess can be determined via chiral gas chromatography. In that case, for the attainment of a high enantiomeric excess, with particular preference the catalyst system should be activated a second time, after the first reductive activation with hydrogen, through the use of an alcohol, such as 1-nonanol, 1,4-butanediol, or citronellol, for example.

With the use of citronellol, for example, enantiomeric excesses of greater than 99% can be achieved; for 1-nonanol, figures of up to 98.4%; and for 1,4-butanediol, figures of up to 93.4%. In the reactions stated, for example, the enantiomer with (R) configuration in position 5 is the preferred enantiomer.

The invention is now elucidated in more detail with reference to nonlimiting examples below.

EXPERIMENTAL SECTION

A) General Working Methods

The reactions below were carried out in a gas-phase apparatus comprising a reactor with double-wall glass tube, with an inner tube which can be heated electrically and contains a perforated plate at the bottom end. The reactor is charged with the catalyst, which is reductively activated by an $H_2$-containing gas stream (20-40 NL/h) at a temperature of 170-180° C. Following the activation of the catalyst, the reactor is operated under inert gas atmosphere, and the nitrogen carrier gas flows through the reactor from top to bottom. The liquid starting materials are transferred to the gas phase using a vaporizer, which is constructed in analogy to the reactor and is mounted above the reactor. The product mixture is condensed by water cooling.

manganese oxide, and 30-40% aluminum copper oxide ($Al_2CuO_4$)) and the catalyst was activated under an $H_2$-containing gas stream (20-40 NL/h) at a temperature of 170-180° C. Vaporizer and reactor were subsequently operated at a temperature of 170'C and with a flow of nitrogen (20 NL/h) under atmospheric pressure. Isopulegol (water content 3.7 wt %, 15 g/h, 97.2 mmol/h) was introduced continuously into the vaporizer. The product mixture was condensed at the reactor exit, and the composition was analyzed by gas chromatography. After a five-hour experiment time in each case, reactor and vaporizer were cooled under a stream of nitrogen (20 NL/h) and the experiment was continued after 18 h without change of catalyst.

The reaction of isopulegol was complete over the entire reaction time.

TABLE 1

Conversion rate, mass balance, and product composition in the reaction of isopulegol.

| Experiment | Time [h] | Conversion of isopulegol [%]* | Selectivity for menthone [%]* | Selectivity for iso-menthone [%]* | Selectivity for menthones (total) [%]* | Selectivity for thymol [%]* | Mass balance [%] |
|---|---|---|---|---|---|---|---|
| 1 | 5 | 100 | 50.4 | 25.6 | 76.0 | 15.4 | 95 |
| 2 | 5 | 100 | 56.6 | 28.0 | 84.6 | 8.5 | >98 |
| 3 | 5 | 100 | 59.2 | 29.3 | 88.5 | 6.3 | 98 |

*Figures based on area percent.

The stated selectivities, conversion rates, and mass balances were determined by gas chromatography, carried out using an Agilent 7890 A gas chromatograph. Enantiomeric excesses were ascertained by means of chiral gas chromatography, using an Agilent 7890 A gas chromatograph.

Gas Chromatography
Instrument: Agilent 7890 A
Column: 50 m CP-Wax, internal diameter 0.32 mm, film thickness 1.2 μm
Eluent nitrogen
Detector: FID, 250° C.
Injection: 0.2 μL, split 100:1
Temperature: start 130° C., 3° C./min to 150° C., 20 min isothermal at 150° C., 10° C./min to 240° C.
Run time: 60 min
Pressure: 46.671 kPa (pressure regulated)
Chiral Gas Chromatography
Instrument: Agilent 7890 A
Column: 30 m BGB-174 S, internal diameter 0.25 mm, film thickness 0.25 μm
Eluent: helium
Detector: FID, 250° C.
Flow rate: 1.5 ml/min (flow regulated)
Injection: 0.2 μL, split 100:1
Temperature: start 60° C., 2° C./min to 80° C., 30 min isothermal at 80° C., 10° C./min to 210° C.
Run time: 53 min

B) Preparation Examples

Example 1

Reaction of Isopulegol

The gas-phase reactor was charged with X540T 1/8 (150 g, 30-40% copper oxide, 10-25% aluminum oxide, 10-25%

Isopulegol is reacted to menthone in good to very good yields of up to 88.5%. For all of the experiments, the ratio of menthone to isomenthone is in the 65/35 to 70/30 (menthone/isomenthone) range (see table 1).

Example 2

Reaction of Enantiomerically Enriched Isopulegol (ee>99%); Activation of the Catalyst with Citronellol The gas-phase reactor was charged with X540T 1/8 (150 g, 30-40% copper oxide, 10-25% aluminum oxide, 10-25% manganese oxide, and 30-40% aluminum copper oxide ($Al_2CuO_4$)) and the catalyst was activated under an $H_2$-containing gas stream (20-40 NL/h) at a temperature of 170-180° C. Vaporizer and reactor were subsequently operated at a temperature of 170° C. and with a flow of nitrogen (20 NL/h) under atmospheric pressure. Isopulegol (ee>99%, water content 3.7 wt %, 15 g/h, 97.2 mmol/h) was introduced continuously into the vaporizer. The product mixture was condensed at the reactor exit, and the composition was analyzed by gas chromatography. After a five-hour experiment time in each case, reactor and vaporizer were cooled under a stream of nitrogen (20 NL/h) and the experiment was continued after 18 h without change of catalyst. Between experiments 6 and 7, the reactor received a flow of citronellol (15 g/h, 96.0 mmol/h) for five hours at 170° C.

TABLE 2

Overview of the product composition in the reaction of isopulegol (ee > 99%).

| Experiment | Time [h] | Conversion of isopulegol [%]* | Menthone Selectivity [%]* | Menthone ee [%] | Isomenthone Selectivity [%]* | Isomenthone ee [%] | Selectivity for menthones (total) [%]* | Selectivity for thymol [%]* | Mass balance [%] |
|---|---|---|---|---|---|---|---|---|---|
| 1 | 5 | 100 | 50.3 | 65.8 | 25.1 | 67.4 | 75.4 | 14.3 | 95 |
| 2 | 5 | 100 | 55.0 | 75.5 | 26.3 | 77.8 | 81.3 | 9.8 | >98 |
| 3 | 5 | 100 | 58.4 | 84.7 | 28.1 | 85.8 | 86.5 | 7.1 | >98 |
| 4 | 5 | 100 | 58.5 | 85.1 | 28.7 | 86.3 | 87.2 | 6.7 | 98 |
| 5 | 5 | 99.5 | 58.3 | 85.8 | 29.1 | 87.4 | 87.4 | 6.7 | >98 |
| 6 | 5 | 97.7 | 58.3 | 89.2 | 29.7 | 90.2 | 88.0 | 6.8 | >98 |
| 7 | 5 | 51.5 | 42.9 | >99 | 24.5 | >99 | 67.4 | 0.8 | >98 |
| 8 | 5 | 35.2 | 34.4 | >99 | 19.9 | >99 | 54.3 | 0.3 | >98 |

*Figures based on area percent.

The conversion rates of isopulegol to menthone (total) rise successively, up to and including experiment 6, to a figure of 88%. A similar picture is seen with the enantiomeric excesses: starting from moderate enantiomeric excesses for experiment 1, there is a subsequent rise observed to up to 90% ee for experiment 6. Following the activation of the catalyst by citronellol, there is in fact a marked fall in the conversion rate (up to 65% of starting materials is unreacted). In experiments 7 and 8, however, surprisingly, the enantiomeric excess is raised to more than 99% (see table 2).

Example 3

Reaction of Enantiomercally Enriched Isopulegol (ee>99%); Activation of the Catalyst with Citronellol The gas-phase reactor was charged with X540T 1/8 (150 g, 30-40% copper oxide, 10-25% aluminum oxide, 10-25% manganese oxide, and 30-40% aluminum copper oxide ($Al_2CuO_4$)) and the catalyst was activated under an $H_2$-containing gas stream (20-40 NL/h) at a temperature of 170-180° C. Vaporizer and reactor were subsequently operated at a temperature of 170° C. and with a flow of nitrogen (20 NL/h) under atmospheric pressure. Isopulegol (ee>99%, water content 3.7 wt %, 15 g/h, 97.2 mmol/h) was introduced continuously into the vaporizer. The product mixture was condensed at the reactor exit, and the composition was analyzed by gas chromatography. After a five-hour experiment time in each case, reactor and vaporizer were cooled under a stream of nitrogen (20 NL/h) and the experiment was continued after 18 h without change of catalyst. Between experiments 1 and 2, the reactor received a flow of citronellol (15 g/h, 96.0 mmol/h) for five hours at 170° C. Before experiment 11, the temperature was increased to 180° C.

TABLE 3

Overview of the product composition in the reaction of isopulegol (ee > 99%).

| Experiment | Time [h] | Conversion of isopulegol [%]* | Menthone Selectivity [%]* | Menthone ee [%] | Isomenthone Selectivity [%]* | Isomenthone ee [%] | Selectivity for menthones (total) [%]* | Selectivity for thymol [%]* | Mass balance [%] |
|---|---|---|---|---|---|---|---|---|---|
| 1 | 5 | 100 | 52.8 | 71.0 | 25.8 | 71.3 | 78.6 | 12.4 | 94 |
| 2 | 5 | 92.8 | 58.3 | 98.3 | 30.1 | 98.6 | 88.4 | 2.4 | >98 |
| 3 | 5 | 92.3 | 58.7 | 98.3 | 30.6 | 98.6 | 89.3 | 2.4 | >98 |
| 4 | 5 | 90.0 | 58.4 | 98.5 | 30.6 | 98.4 | 89.0 | 2.4 | >98 |
| 5 | 5 | 89.4 | 58.4 | 98.3 | 30.7 | >99 | 89.1 | 2.3 | >98 |
| 6 | 5 | 87.6 | 57.9 | 98.5 | 30.4 | 98.6 | 88.3 | 2.0 | >98 |
| 7 | 5 | 86.6 | 57.7 | 98.6 | 30.3 | 98.7 | 88.0 | 2.0 | >98 |
| 8 | 5 | 84.1 | 57.1 | 98.8 | 30.0 | >99 | 87.1 | 1.7 | >98 |
| 9 | 5 | 82.6 | 56.5 | 98.9 | 29.7 | >99 | 86.2 | 1.6 | >98 |
| 10 | 5 | 78.8 | 55.5 | 99.0 | 29.2 | >99 | 84.7 | 1.4 | >98 |
| 11** | 5 | 89.0 | 57.1 | 98.2 | 30.2 | >99 | 87.3 | 2.3 | >98 |
| 12** | 5 | 87.7 | 56.6 | 98.3 | 30.0 | 98.6 | 86.6 | 2.2 | >98 |

*Figures based on area percent;
**reaction temperature 180° C.

By activating the catalyst with citronellol, it was possible in this case as well to raise the enantiomeric excesses from experiment 2 to greater than 98%. The fall in conversion rate to below 80% in experiment 10 was compensated, surprisingly, by a moderate increase in temperature, by 10° C. High enantiomeric excesses are therefore not necessarily achieved at the expense of the conversion rate (see table 3).

Example 4

Reaction of Enantiomerically Enriched Isopulegol (ee>99%); Activation of the Catalyst with 1-nonanol The gas-phase reactor was charged with X540T 1/8 (75 g, 30-40% copper oxide, 10-25% aluminum oxide, 10-25% manganese oxide, and 30-40% aluminum copper oxide ($Al_2CuO_4$)) and the catalyst was activated under an $H_2$-containing gas stream (20-40 NL/h) at a temperature of 170-180° C. The reactor subsequently received a flow of 1-nonanol (7.5 g/h, 52.0 mmol/h). Vaporizer and reactor were subsequently operated at a temperature of 170° C. and with a flow of nitrogen (20 NL/h) under atmospheric pressure. Isopulegol (ee>99%, water content 3.7 wt %, 7.5 g/h, 48.6 mmol/h) was introduced continuously into the vaporizer. The product mixture was condensed at the reactor exit, and the composition was analyzed by gas chromatography.

TABLE 4

Overview of the product composition in the reaction of isopulegol (ee > 99%) with the catalyst activated with 1-nonanol.

| Experiment | Time [h] | Conversion of isopulegol [%]* | Menthone Selectivity [%]* | ee [%] | Isomenthone Selectivity [%]* | ee [%] | Selectivity for menthones (total) [%]* | Selectivity for thymol [%]* | Mass balance [%] |
|---|---|---|---|---|---|---|---|---|---|
| 1 | 5 | 96.8 | 56.8 | 98.2 | 32.1 | 98.4 | 88.9 | 3.3 | >98 |

*Figures based on area percent.

The treatment of the hydrogen-activated catalyst with 1-nonanol leads to menthone in enantiomerically enriched form in the case of high conversion rates. For the use of this alcohol as well, surprisingly, it is possible to achieve enantiomeric excesses of more than 98% (see table 4).

Example 5

Reaction of Enantiomercally Enriched Isopulegol (ee>99%); Activation of the Catalyst with 1,4-butanediol The gas-phase reactor was charged with X540T 1/8 (75 g, 30-40% copper oxide, 10-25% aluminum oxide, 10-25% manganese oxide, and 30-40% aluminum copper oxide ($Al_2CuO_4$)) and the catalyst was activated under an Hz-containing gas stream (20-40 NL/h) at a temperature of 170-180° C. The reactor subsequently received a flow of 1,4-butanediol (7.5 g/h, 83.2 mmol/h). Vaporizer and reactor were subsequently operated at a temperature of 170° C. and with a flow of nitrogen (20 NL/h) under atmospheric pressure. Isopulegol (ee>99%, water content 3.7 wt %, 7.5 g/h, 48.6 mmol/h) was introduced continuously into the vaporizer. The product mixture was condensed at the reactor exit, and the composition was analyzed via gas-chromatographic studies.

TABLE 5

Overview of the product composition in the reaction of isopulegol (ee > 99%) with the catalyst activated with 1,4-butanediol.

| Experiment | Time [h] | Conversion of isopulegol [%]* | Menthone Selectivity [%]* | ee [%] | Isomenthone Selectivity [%]* | ee [%] | Selectivity for menthones (total) [%]* | Selectivity for thymol [%]* | Mass balance [%] |
|---|---|---|---|---|---|---|---|---|---|
| 1 | 5 | 96.1 | 56.5 | 93.0 | 28.8 | 93.4 | 85.3 | 1.8 | >98 |

*Figures based on area percent.

The treatment of the hydrogen-activated catalyst with 1,4-butanediol likewise results in good conversion rates of isopulegol to menthone. The enantiomeric excesses, however, remain slightly behind the results achieved for 1-nonanol and citronellol. The suitability of diols for this reaction was nevertheless successfully demonstrated (see table 5).

Example 6

Reaction of Enantiomerically Enriched Isopulegol (ee>99%); Activation of the Catalyst with 3-pentanol The gas-phase reactor was charged with X540T 1/8 (75 g, 30-40% copper oxide, 10-25% aluminum oxide, 10-25% manganese oxide, and 30-40% aluminum copper oxide ($Al_2CuO_4$)) and the catalyst was activated under an $H_2$-containing gas stream (20-40 NL/h) at a temperature of 170-180° C. The reactor subsequently received a flow of 3-pentanoi (7.5 g/h, 85.1 mmol/h). Vaporizer and reactor were subsequently operated at a temperature of 170° C. and with a flow of nitrogen (20 NL/h) under atmospheric pressure. Isopulegol (ee>99%, water content 3.7 wt %, 7.5 g/h, 48.6 mmol/h) was introduced continuously into the vaporizer. The product mixture was condensed at the reactor exit, and the composition was analyzed by gas chromatography.

TABLE 6

Overview of the product composition in the reaction of isopulegol (ee > 99%) with the catalyst activated with 3-pentanol.

| Experiment | Time [h] | Conversion of isopulegol [%]* | Menthone Selectivity [%]* | ee [%] | Isomenthone Selectivity [%]* | ee [%] | Selectivity for menthones (total) [%]* | Selectivity for thymol [%]* | Mass balance [%] |
|---|---|---|---|---|---|---|---|---|---|
| 1 | 5 | 100 | 48.5 | 70.2 | 24.6 | 71.6 | 73.1 | 10.7 | 89 |
| 2 | 24 | 100 | 52.3 | 80.5 | 27.0 | 81.5 | 79.3 | 8.3 | 93 |
| 3 | 24 | 93.4 | 54.7 | 91.1 | 30.6 | 92.6 | 85.3 | 4.6 | 95 |
| 4 | 4 | 88.9 | 52.6 | 94.9 | 30.8 | 96.0 | 83.4 | 2.9 | 96 |

*Figures based on area percent.

Following treatment of the catalyst with 3-pentanol, isopulegol can be reacted with a high conversion rate and high selectivity to form menthone/isomenthone. The enantiomeric excess is not immediately >90%, but does rise from an initial figure of about 70% to about 95% over the course of 52 hours.

Example 7

Reaction of Enantiomerically Enriched Isopulegol (ee>99%); Activation of the Catalyst with Isopropanol The gas-phase reactor was charged with X540T 1/8 (50 g, 30-40% copper oxide, 10-25% aluminum oxide, 10-25% manganese oxide, and 30-40% aluminum copper oxide ($Al_2CuO_4$)) and the catalyst was activated under an $H_2$-containing gas stream (20-40 NL/h) at a temperature of 170-180° C. The reactor subsequently received a flow of isopropanol (5 g/h, 83.2 mmol/h). Vaporizer and reactor were subsequently operated at a temperature of 170° C. and with a flow of nitrogen (20 NL/h) under atmospheric pressure. Isopulegol (ee>99%, water content 3.7 wt %, 5 g/h, 32.4 mmol/h) was introduced continuously into the vaporizer. The product mixture was condensed at the reactor exit, and the composition was analyzed via gas-chromatographic studies.

TABLE 7

Overview of the product composition in the reaction of isopulegol (ee > 99%) with the catalyst activated with isopropanol.

| Experiment | Time [h] | Conversion of isopulegol [%]* | Menthone Selectivity [%]* | ee [%] | Isomenthone Selectivity [%]* | ee [%] | Selectivity for menthones (total) [%]* | Selectivity for thymol [%]* | Mass balance [%] |
|---|---|---|---|---|---|---|---|---|---|
| 1 | 5 | 99.2 | 51.9 | 81.9 | 26.8 | 83.9 | 78.7 | 7.8 | 89 |

*Figures based on area percent.

Following treatment with isopropanol, menthone was obtained from isopulegol with high conversion rate and high selectivity. The enantiomeric excess was constant from the third hour of experimentation onward, at just above 80%.

Example 8

Reaction of Enantiomercally Enriched Isopulegol (ee>99%); Activation of the Catalyst with 1,3-butanediol The gas-phase reactor was charged with X540T 1/8 (50 g, 30-40% copper oxide, 10-25% aluminum oxide, 10-25% manganese oxide, and 30-40% aluminum copper oxide ($Al_2CuO_4$)) and the catalyst was activated under an $H_2$-containing gas stream (20-40 NL/h) at a temperature of 170-180° C. The reactor subsequently received a flow of 1,3-butanediol (5 g/h, 55.5 mmol/h). Vaporizer and reactor were subsequently operated at a temperature of 170° C. and with a flow of nitrogen (20 NL/h) under atmospheric pressure. Isopulegol (ee>99%, water content 3.7 wt %, 5 g/h, 32.4 mmol/h) was introduced continuously into the vaporizer. The product mixture was condensed at the reactor exit, and the composition was analyzed via gas-chromatographic studies.

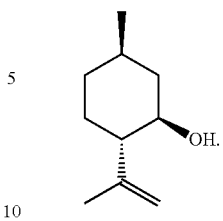

TABLE 8

Overview of the product composition in the reaction of isopulegol (ee > 99%) with the catalyst activated with 1,3-butanediol.

| Experiment | Time [h] | Conversion of isopulegol [%]* | Menthone Selectivity [%]* | Menthone ee [%] | Isomenthone Selectivity [%]* | Isomenthone ee [%] | Selectivity for menthones (total) [%]* | Selectivity for thymol [%]* | Mass balance [%] |
|---|---|---|---|---|---|---|---|---|---|
| 1 | 5 | 34.3 | 18.2 | >99 | 11.9 | >99 | 30.1 | 0 | 93 |
| 2** | 5 | 85.6 | 39.4 | 98.2 | 24.7 | 97.7 | 64.1 | 0.8 | 92 |

*Figures based on area percent;
**reaction temperature 190° C.

The enantioselectivity achieved on activation using 1,3-butanediol was greater than 99% for the reaction products menthone and isomenthone, with an initially low conversion rate and low selectivity at 170° C. By increasing the temperature to 190° C. from hour 6, however, it was possible to raise conversion rate and selectivity, still always with a high ee (>97%).

The disclosure content of documents cited herein is referred to in its entirety.

We claim:

1. A process for making menthone comprising contacting a carrier gas that includes isopulegol in the gas phase with an activated oxidic copper catalyst, optionally comprising at least one element selected from aluminum, manganese, barium, chromium, calcium, or iron, and optionally isolating a menthone-containing reaction product.

2. The process according to claim 1, wherein a copper catalyst is activated with hydrogen, or with hydrogen and an alcohol to form the activated oxidic copper catalyst.

3. The process according to claim 1, wherein the activated, oxidic copper catalyst includes copper present in the +I or +II oxidation state.

4. The process according to claim 1, wherein the carrier gas comprises nitrogen, argon or a mixture thereof.

5. The process according to claim 1, wherein the isopulegol comprises an enantiomer of the formula I 6. The process according to claim 1, wherein the reaction is carried out at a temperature of 150-250° C.

7. The process according to claim 1, wherein the activated, oxidic copper catalyst comprises copper and at least one further element selected from aluminum, manganese, barium, chromium, calcium, or iron, each in elemental form and/or as oxides.

8. The process according to claim 7, in which the oxides are present as single-element oxides, double oxides, multiple oxides, or mixtures thereof.

9. The process according to claim 1, wherein the activated, oxidic copper catalyst has a fraction of at least 20% up to 100 wt % of copper compound, based on the dry mass of the catalyst.

10. The process according to claim 1, wherein the activated, oxidic copper catalyst is selected from one of the following compositions:
a) 30-40% copper oxide, 10-25% aluminum oxide, 10-25% manganese oxide, and 30-40% aluminum copper oxide,
b) 30-45% copper oxide, 10-25% aluminum oxide, 10-20% manganese oxide, and 30-40% aluminum copper oxide,
c) 60.0-65.0% chromium copper oxide ($Cr_2CuO_4$), 20.0-25.0% copper oxide, 5.0-10.0% barium oxide, 1,0-5.0% graphite, 1.0% dichromium trioxide, and 1.0% chromium trioxide,
d) 60.0-70.0% chromium copper oxide ($Cr_2CuO_4$), 20.0-30.0% copper oxide, 1.0-5.0% manganese dioxide, 1.0-5.0% silicic acid (sodium salt), 1.0-5.0% graphite, and 0.0-0.5% copper chromate,
e) 55.0-65.0% chromium copper oxide ($Cr_2CuO_4$), 20.0-30.0% copper oxide, 5.0-10.0% silicon dioxide, 5.0-10.0% silicic acid (sodium salt), and 1.0-5.0% graphite,
f) 41.0-46.0% chromium copper oxide ($Cr_2CuO_4$), 25.0-35.0% aluminum oxide, 13.0-17.0% copper oxide, and 10.0-13.0% barium chromate,
g) 55.0-65.0% copper oxide, 25.0-35.0% calcium silicate, 5.0-10.0% palygorskite ($[Mg(Al_{0.5}-1Fe_{0-0.5})]Si_4(OH)$ $O_{10}.4H_2O$ ), 1.0-5.0% graphite, 1.0-5.0% silicon dioxide, and 0.5-1.5% silica (crystalline), or h) any one mixture of catalyst compositions a) to g), in each case in wt %, based on the dry mass of the catalyst.

11. The process according to claim 2, wherein the catalyst is activated with hydrogen and an alcohol, added simultaneously or one before the other, in any order, optionally with a carrier gas stream.

12. The process according to claim 11, in which the carrier gas is nitrogen or argon and optionally comprises up to 10 vol % of hydrogen.

13. The process according to claim 11, wherein the alcohol used for the activation is selected from saturated or mono- or polyunsaturated, straight-chain or branched or cyclic, aliphatic or aromatic monools or polyols, or combinations thereof.

14. The process according to claim 11, wherein the alcohol used for the activation comprises at least one primary and/or secondary OH group.

15. The process according to claim 13 wherein the alcohol is a $C_3$-$C_{16}$ alcohol.

16. The process according to claim 5, wherein the reaction product comprises menthone and/or isomenthone with a fraction of more than 80% of the enantiomer with (R) configuration at the methyl carbon.

17. The process according to claim 1, wherein the reaction product menthone and/or isomenthone is present in at least 99% enantiomerically pure form.

18. The process according to claim 1, wherein the oxidic copper catalyst comprises a double mixed oxide selected from 30%-40% aluminium copper oxide, or 41% to 70% chromium copper oxide.

19. A process for making menthone comprising contacting a carrier gas that includes isopulegol in the gas phase with an activated oxidic copper catalyst, the copper catalyst activated with hydrogen, or with hydrogen and an alcohol, and optionally comprising at least one metal selected from aluminum, manganese, barium, chromium, calcium, or iron, each metal as an oxide, elemental form, or a mixture thereof, to provide a menthone-containing reaction product that includes menthone and isomenthone, each with at least 80% stereoselectivity of (R) configuration at the methyl carbon.

20. A method of producing a consumer product comprising menthone additive, wherein the menthone additive is produced by a process comprising contacting a carrier gas that includes isopulegol in the gas phase with an activated oxidic copper catalyst, the catalyst optionally comprising at least one element selected from aluminum, manganese, barium, chromium, calcium, or iron, isolating a menthone-containing reaction product (methone additive), and adding the menthone additive to the consumer product selected from the group consisting of foods, cosmetics, pharmaceutical products, tobacco formulations, household products, and laundry care products.

21. The method of claim 20, wherein the menthone product that is added to the consumer product includes menthone and isomenthone, each with at least 80% stereoselectivity of (R) configuration at the methyl carbon.

* * * * *